United States Patent [19]

Culkin

[11] Patent Number: 4,679,439
[45] Date of Patent: Jul. 14, 1987

[54] METHOD AND APPARATUS FOR MEASURING THE UNSTEADY SEDIMENTATION POTENTIAL OF COLLOIDAL PARTICLES

[75] Inventor: Joseph B. Culkin, Wilton, Conn.

[73] Assignee: Dorr-Oliver Incorporated, Stamford, Conn.

[21] Appl. No.: 777,101

[22] Filed: Sep. 17, 1985

[51] Int. Cl.⁴ .............................................. G01N 27/00
[52] U.S. Cl. ..................................... 73/61.4; 324/71.1
[58] Field of Search ...................... 73/61 R, 61.4, 64.1, 73/53, 432 PS; 324/71.1, 450, 439; 210/796; 204/180.1, 183.1, 183.3, 183.7; 422/68, 73; 436/70; 366/237

[56] References Cited

U.S. PATENT DOCUMENTS

| | | | |
|---|---|---|---|
| 2,874,841 | 2/1959 | Peterson | 366/237 |
| 3,254,527 | 6/1966 | Noller | 73/61.4 |
| 3,457,791 | 7/1969 | Johnson et al. | 73/38 |
| 3,533,934 | 10/1970 | Armanini | 204/180.1 |
| 3,635,678 | 1/1972 | Seitz et al. | 73/57 |
| 3,722,591 | 11/1973 | Louder et al. | 436/70 |
| 3,756,400 | 9/1973 | Kammori et al. | 73/432 PS |
| 3,917,451 | 11/1975 | Groves et al. | 324/71.1 |
| 4,090,937 | 5/1978 | Stoev et al. | 204/180.1 |
| 4,191,047 | 3/1980 | Arrigoni et al. | 73/61.4 |
| 4,278,437 | 7/1981 | Haggar | 73/64.1 |
| 4,446,435 | 5/1984 | Canzoneri | 324/71.1 |
| 4,497,208 | 2/1985 | Oja et al. | 73/61 R |
| 4,535,285 | 8/1985 | Evans et al. | 324/71.1 |
| 4,602,989 | 7/1986 | Culkin | 204/183.3 |

FOREIGN PATENT DOCUMENTS 968706 10/1982 U.S.S.R. ............................. 73/61.4

Primary Examiner—Stewart J. Levy
Assistant Examiner—Hezron E. Williams
Attorney, Agent, or Firm—Burtsell J. Kearns

[57] ABSTRACT

A method and apparatus for measuring the unsteady sedimentation potential of particle in a suspension comprising: inserting at least a portion of the suspension of particles in a cell, the cell having a first electrode and a second electrode; vibrating the cell to accelerate the particles in suspension; and measuring the unsteady sedimentation potential of the particles across the first and second electrodes. The cell is vibrated at a frequency in the range between 0.0001–50 khz.

25 Claims, 2 Drawing Figures

METHOD AND APPARATUS FOR MEASURING THE UNSTEADY SEDIMENTATION POTENTIAL OF COLLOIDAL PARTICLES

BACKGROUND OF THE INVENTION

The present invention relates to a novel method and apparatus for measuring the unsteady sedimentation potential of particles in a suspension comprising: a cell which has at least a portion of the suspension of particles inserted therein; a first electrode and a second electrode disposed within the cell; means for vibrating the cell to accelerate the particles of suspension within the cell; and measuring the amplitude of the unsteady sedimentation potential of the particles across the first and second electrodes, for example, by means of a synchronous demodulator. In particular, the present invention provides for the vibration of the cell at a frequency in the range between 0.0001–50 khz.

Determination of the zeta potential of particles in a suspension is very helpful in controlling the addition of auxiliary agents to influence the flocculation and retention characteristics of particles. The addition of auxiliary agents can substantially influence the zeta potential and it is for this reason that much time has been devoted to methods and apparatuses to be used in determining the zeta potential of colloidal particles.

Many attempts have been made at measuring the zeta potential among them the use of ultrasonic sound to measure the vibration potential between two electrodes, and application of a laser beam and optical measurement thereof to determine the electrophoretic mobility of the migrating particles. The use of ultrasonic sound to measure the vibration potential of particles in suspension is disclosed in U.S. Pat. Nos. 4,294,656, 4,381,674 and 4,497,208.

U.S Pat. No. 4,294,656 provides for a process for measuring zeta potential wherein a portion of the suspension is exposed to an ultrasonic sound field in a measuring cell, the measuring cell having two electrodes which extend into the suspension and are spaced from each other by an odd multiple of half ultrasonic wave lengths of the ultrasonic sound field in the suspension, and generating a signal from the voltage thereby formed between the electrodes which corresponds to the state of charge and determines the addition of auxiliary agent.

U.S. Pat. No. 4,381,674 discloses a method of detecting and identifying particulates in the recycling fluid flow of an oil recovery system by counting the number of ultrasonic pulses reflected from the particulates and comparing the number counted with the amount of ultrasonic energy across the flow.

U.S. Pat. No. 4,497,208 discloses a method and apparatus for measuring electro-kinetic properties of charged particles dispersed in a liquid medium which comprises the step of positioning two electrodes to contact the liquid medium, energizing the electrodes with an alternating electrical potential to cause a charged separation between the surfaces of the dispersed particles and the charged layers which surround the particles in the liquid medium and thereby to generate an acoustic signal, spacing an acoustic transducer from the electrodes for detecting an acoustic signal, and measuring the amplitude of the detected signal, the amplitude of the detected signal apparently being a function of the electro-kinetic properties of the particles present in the liquid medium, the number of particles per unit volume and the amplitude of the excitation potential on the electrodes.

Another means of measuring the zeta potential of colloidal particles is described in U.S. Pat. No. 4,046,667 which provides for a microelectrophoresis apparatus for measuring the zeta potential or electrophoretic mobility of particles suspended in a bulk medium, e.g. colloids suspended in a liquid. It further provides for the use of a light beam, microscope and objective lens system for physically determining the zeta potential of colloidal particles. The use of the microscope and requires a highly trained technician to physically determine the zeta potential on a periodic basis. This system is inherently subject to human error and also requires prolonged analysis prior to each measurement.

The aforementioned patents relate either to the measuring of a vibration potential by use of ultrasonic sound in a frequency range of above 100 khz, or to the measurement of electrophoretic mobility by the use of optical methods. Ultrasonic methods which measure a so-called "vibration potential" suffer from a lack of adequate theory linking vibration potential measurements to familiar colloidal properties such as zeta potential. The optical methods suffer from complexity and human error in the measurement of electrophoretic mobility.

It is known that the application of an electric field causes charged particles in a slurry to migrate. Conversely, the migration of charged particles under the action of a body force, such as gravity (this is called sedimentation), will result in the creation of an electric field. The potential difference which arises between separate points in such a system is called the sedimentation potential.

Attempts have been made to measure the sedimentation potential but most are disappointing because steady forces, such as gravity, produce extremely small, steady sedimentation potentials. Small, steady sedimentation potentials are hard to detect due to the occurrence of drift in the electronics, and due to assymmetry potentials which arise at the electrodes which must be introduced into the liquid for purposes of measurement.

The application of unsteady (time-periodic) forces to colloidal particles has been limited historically to ultrasound frequencies above 100 khz as demonstrated in U.S. Pat. Nos. 4,294,656, 4,381,674 and 4,497,208. The principles underlining the aforementioned patents suggests that the colloidal particles are induced to vibrate relative to the liquid due to an interaction with ultrasonic sound waves which are applied to the slurry. The particles vibrate in sympathy with the passage of the ultrasound wave because the sound speed inside the particle is different from the sound speed in the surrounding liquid. An electric potential will exist between two electrodes placed one half wave length apart in the slurry, and this potential is reportedly linked to the zeta potential of the particles. However, no satisfactory theoretical model exists to predict the exact relationship between this acoustic vibration potential measured and zeta potential. Thus, the accuracy of determining the zeta potential using ultrasonic sound frequencies has been found to be unreliable and theoretically unproven.

The present inventor has devised a novel method and apparatus which overcomes the deficiencies of the prior art. Moreover, the present invention provides a method and apparatus for detecting the unsteady sedimentation potential of particles in a suspension which is directly proportionally to the zeta potential of the colloidal particles.

The advantages of the method and apparatus according to the present invention will be further described below.

SUMMARY OF THE INVENTION

It is the primary object of the present invention to provide a method and apparatus for determining the zeta potential of particles in suspension. The method comprising inserting at least a portion of the suspension of particles in a cell, the cell having a first electrode and a second electrode; vibrating the cell to accelerate the particles in suspension; and measuring the unsteady sedimentation potential of the particles across the first and second electrodes.

Furthermore, it is an object of the present invention to provide an apparatus for determining the zeta potential of particles in suspension comprising: a cell, the cell containing at least a portion of particles in suspension therein; a first electrode and a second electrode disposed within the cell; means for vibrating the cell to accelerate the particles in suspension; and means for detecting an unsteady sedimentation potential of the particles across the first and second electrodes. It is preferable according to the present invention to provide that the first and second electrodes be disposed at opposite ends of the cell.

Additionally, it is an object of the present invention that the cell be vibrated by means of a motor, e.g., a speaker motor. It is also preferable that a mechanical resonator, such as a tuning fork, having a frequency range between 0.0001–50 khz be disposed between the speaker motor and the cell. For this reason, the cell will vibrate in the frequency range between 0.0001–50 khz. The speaker motor is connected to either the cell or the mechanical resonator by mechanical linkage, such as a steel rod. Similarly, the mechanical resonator is connected to both the motor and the cell by means of a steel rod. It is also an object of the present invention that if only a motor is used to vibrate the cell that the motor operate in a frequency range between 0–50 khz.

It is a further object of the present invention that the vibration of the cell results in acceleration of the particles which in turn causes an unsteady sedimentation potential across the first and second electrodes of the cell. The unsteady sedimentation potential being measured by an amplitude detector, such as a synchronous demodulator. A further object of the present invention is that the amplitude detector has a detecting frequency in a range between 0–50 khz. An amplifier may be disposed between the electrodes and the amplitude detector to amplify the signal produced by the unsteady sedimentation potential since it is a very small signal which is being measured.

The present invention may also include many additional features which shall be further described below.

DESCRIPTION OF THE PREFERRED EMBODIMENT

Figure 1:
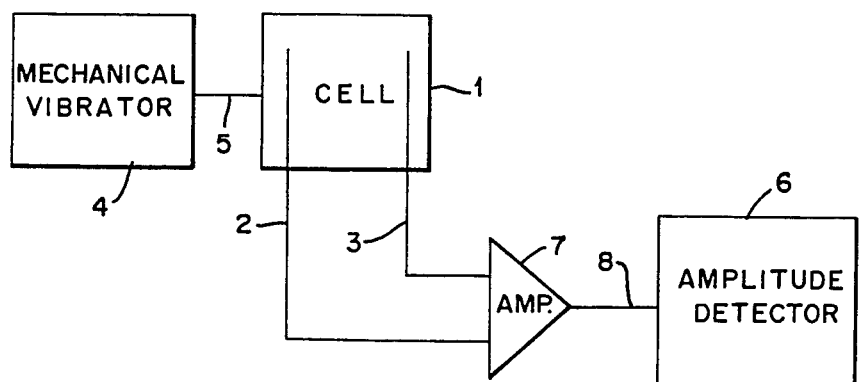
FIG. 1 is a block diagram depicting the present invention.

The present invention provides a novel method and apparatus which detects the unsteady sedimentation potential caused by the acceleration of the particles in suspension between a first and second electrode disposed within a cell. Accordingly, the unsteady sedimentation potential measured by the present invention is directly proportional to the zeta potential of the colloidal particles of suspension. The unsteady sedimentation potential can be easily detected (demodulated) using extremely accurate A-C signal detection techniques, e.g. synchronous demodulators. It has been found by the present inventor that it is important to limit the frequency of operation to a range between 0.001–50 khz, so that the unsteady acceleration of the cell will result in a rigid body translation of the entire cell contents. If frequencies in excess of 50 khz are attempted, the motion can no longer be described as a homogeneous acceleration of the liquid in the cell. Rather, the system must be described using an acoustic wave model similar to that used in measuring the so-called "vibration potential" which is treated in the prior art. This distinction, between a slowly accelerated cell undergoing a rigid body translational acceleration, and the acoustic wave system used by others serves to separate this invention from the prior art.

The zeta potential is particularly important when solids, such as kaolin clay particles, are placed into an electrolyte solution (sodium sulfate or other salts), the surface of the solids often becomes charged up relative to the bulk salt solution. Typically, this charging up of the solid surface is due to adsorption of one or several ions of a particular charge. Kaolin clay, for instance, tends to be an anion exchange material, that is, the clay particles tend to adsorb anions on its surface to neutralize immobile cationic exchange sites. The adsorption of anions on to the clay particles tends to make the particles become negatively charged. The charging of the small particles, i.e. less than 10 microns in diameter, is very important in determining the macroscopic behavior of a slurry of such particles. Such slurries occur in a wide variety of systems including paints, pigments, coal slurries, pulp and paper manufacture, and many others.

The region of liquid near a charged solid surface in contact with electrolytes is called a diffuse double layer. In this region, two counterposed effects are in balance. On the one hand, ions, for example, cations, want to move towards the solid surface to join the adsorbed anions and thus produce a neutral space-charge distribution. On the other hand, cations mutually repel one another, and spontaneous aggregation of cations in one region of space near the particle constitutes a concentration gradient which tends to be reduced by diffusion away from the solid surface. The equilibrium distribution of cations outside the region of adsorbed anions is the result of a superposition of all these effects. The electrical potential distribution which exists inside the double layer is roughly exponential in shape.

Thus, when electric fields are applied to the charged bodies, forces act on the charged bodies. The relationship being:

$$F = Eq \qquad (1)$$

where F is the force, E is the electric field strength and q is the charge.

A particle in an electrolyte within an applied electric field will result in having a force couple acting to move the minus charges attached to the particle in one direction, and there will be opposing forces acting to move the plus charged liquid surrounding the particle and double layer in the opposite direction. Thus, there is a net migration of particles in one direction and liquid in the opposite direction. An unsteady electric field causes the particles of suspension to accelerate.

To define the zeta potential of a colloidal particle in suspension one must first determine that distribution of charge near the particle by the following equations: (1) Poisson's equations which relates charge density to electric potential; (2) the Poisson-Boltzman's equation which balances the desire of cations to join with anions against diffusion forces which resist the aggregation of cations into one region of space; (3) Ohm's law which relates the electric field strength to the conductivity of the electrolyte; and (4) the momentum equation where F=ma as applied to the liquid surrounding the particle and applied to the particle itself. These equations determine how colloidal particles will react to the application of electric fields, e.g. by passing currents through a slurry.

To solve the system of coupled partial differential equations, one must apply boundary conditions. Thus, equations 1 and 2 above require the specification of a potential someplace near the solid surface. Equation 4 above requires that a no-slip condition be applied at the "shear-plane", where the "liquid" outer region of the ion cloud surrounding a particle becomes "solid" in nature, and shear is no longer allowed. The potential is often specified at a location coincident with the place where the no-slip condition is imposed. This potential is then defined as the zeta potential.

Zeta potential is used in practice as a measure of the amount of charge adsorbed onto the particles in a suspension. Consider the case where a suspension of colloidal particles is settling or sedimenting out under the action of gravity. In such a case, charged colloidal particles are seen to migrate with a constant velocity toward the bottom of the vessel which contains the slurry. This movement of charge associated with the migrating particles constitutes a small electric current which in turn produces a small electric field. This electric field can be detected by inserting two electrodes spaced along the direction of migration of the particles. The potential detected by the electrodes is called the sedimentation potential ($E_{sed}$).

$$E_{sed} = \frac{\epsilon Z}{3\mu\lambda} R^3 (\rho_p - \rho_e) c g \quad (2)$$

where
$E = \epsilon_o D$
$\epsilon_o$ = permitivity of free space
$D$ = dielectric constant of liquid
$\mu$ = fluid viscosity.
$\lambda$ = fluid conductivity.
$R$ = particle radius.
$\rho_p$ = particle density.
$\rho_e$ = liquid density.
$C$ = particle concentration. No. of particles/unit volume.
$g$ = acceleration due to gravity.
$z$ = zeta potential.
$E_{sed}$ = sedimentation potential.

The steady acceleration of gravity produces a steady sedimentation potential which is extremely hard to detect because other steady potentials also exist due to non-sedimentation related effects. To make the sedimentation potential more easily detected, the present inventor applies an unsteady acceleration to the entire system by vibrating the entire cell at a convenient frequency, e.g. 1 khz. The theory for sedimentation potential is then modified by substituting $g = A \sin \omega t$ in the equation for sedimentation potential, where A is the amplitude of the externally applied unsteady acceleration, $\omega$ is the frequency of the unsteady acceleration, and t is time. Thus, $$E_{used} = \frac{\epsilon Z}{3\mu\lambda} R^3 (\rho_p - \rho_e) CA \, \text{SIN} \, \omega t \quad (3)$$

where
$E_{used}$ is the unsteady sedimentation potential.

The dependency here between the unsteady sedimentation potential and the particle radius can be eliminated by noting that for any particle size $R_n$, the quantity:

$$\rho_p \frac{4}{3} \pi \sum_n^{c_n} R_n^3 \quad (4)$$

is the mass of particles of size $R_n$, where n is a dummy index and $c_n$ is the number of particles of size $R_n$. We can therefore write that:

$$E_{used} = \frac{\epsilon Z(\rho_p - \rho_e)}{4\pi\mu\lambda\rho_p} A \, \text{SIN} \, \omega t \, C_p \quad (5)$$

where $C_p$ is the mass concentration of all particles in g/cm$^3$.

The action of the synchronous amplitude detector in the present invention is to give the average value of the signal amplitude that is strictly proportional to the quantity $A \sin \omega t$, over time and to reject noise at other frequencies. Thus we can define an average synchronously detected unsteady sedimentation potential as:

$$\overline{E}_{used} = \frac{1}{T} \int_0^T \text{SIN} \, \omega t \, E_{used} \, dt \quad (6)$$

where
T is the averaging interval. Thus, $$\overline{E}_{used} = \frac{\epsilon Z(\rho_p - \rho_e) A C_p}{\mu\lambda 8\pi\rho_p} \quad (7)$$

Clearly, this equation can be inverted to find zeta:

$$Z = \frac{(\overline{E}_{used})\mu\lambda 8\pi\rho_p}{\epsilon(\rho_p - \rho_e)C_p}$$

where
$\overline{E}_{used}$ is measured by the amplitude detector of the present device and the remaining values are constant as listed below:
$\mu$ = constant liquid viscosity.
$\lambda$ = constant liquid conductivity.
$\epsilon$ = a material constant.
$\rho_p$ = constant particle density.
$\rho_e$ = constant liquid density.
$A$ = known amplitude of the applied acceleration.
$C_p$ = known mass concentration of the particles in the slurry.

The present invention, as shown in FIG. 1, has a cell 1 having a pair of electrodes 2 and 3 disposed therein. A suspension of particles is inserted into cell 1 for measuring the unsteady sedimentation potential caused due to acceleration of the particles in cell 1 which in turn is caused by the vibration of cell 1 by means of a mechanical vibrator or motor 4. The motor 4 may be a speaker motor which is connected to cell 1 by means of mechanical linkage 5, such as a steel rod.

As the particles in cell 1 are caused to accelerate by means of motor 4 at a frequency between 0.001–50 khz an unsteady sedimentation potential occurs between electrodes 2 and 3 which is detected by amplitude detector 6. Amplitude detector 6 is preferably a synchronous demodulator. It is also preferable that an amplifier 7 be disposed between electrodes 2 and 3 and amplitude detector 6. Amplifier 7 is connected to amplitude detector 6 via wire 8. The unsteady sedimentation potential measured by amplitude 6 is directly proportional to zeta.

Figure 2:
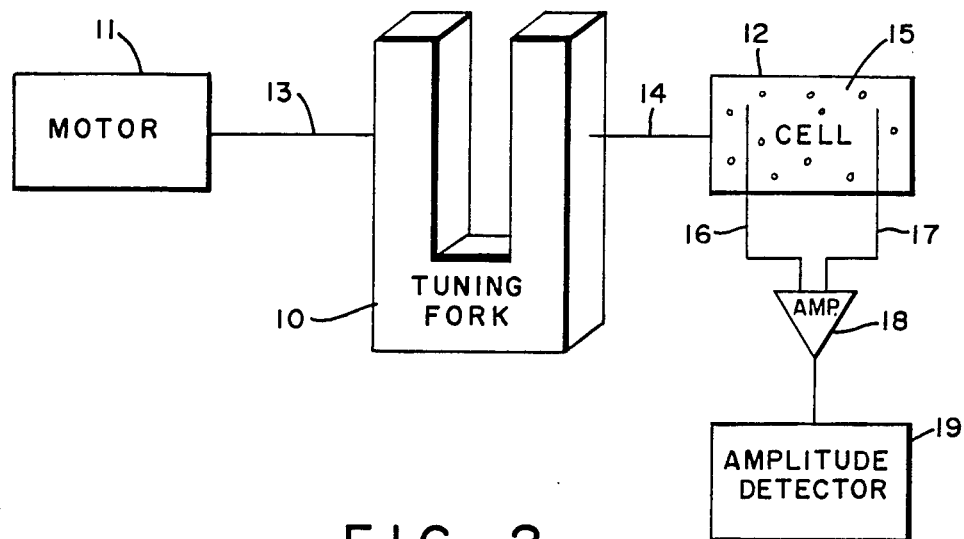
FIG. 2 is a block diagram describing the preferred embodiment according to the present invention.

FIG. 2 is a preferred embodiment according to the present invention wherein a mechanical resonator, such as tuning fork 10, is disposed between motor 11 and cell 12 via mechanical linkages 13 and 14. In operation, cell 12 is vibrated at a frequency in the range between 0.0001–50 khz by tuning fork 10. In this frequency range, the cell 2 and the suspension of particles 15 contained within cell 12 move essentially as a rigid body in translation. Electrodes 16 and 17 detect the unsteady sedimentation potential which exist due to the sinusoidal acceleration of cell 12. If cell 12 is driven by tuning fork 10, as shown in FIG. 2, at exactly 1 khz, the output from cell 12 will be exactly 1 khz. Taking advantage of this fact, we can use a very narrow band detection means, such as a synchronous demodulator 19, an amplifier 18 may be also incorporated between the synchronous demodulator 19 and electrodes 16 and 17.

In the preferred embodiment of the present invention, the tuning fork 10 is used to act as an impedance matching device between the motor 11 and cell 12. That is, the tuning fork 10 can be chosen to operate at a specific resonant frequency. This allows use of a much smaller motor 11 to drive cell 12 to large accelerations of the particles in suspension 15. However, it should be kept in mind that the tuning fork 10 is not necessarily required and that cell 12 could be hooked directly to a linear motor 4, as shown in FIG. 1. However, a large linear motor would be required to attain the same acceleration amplitude as those made possible by use of a tuning fork 10.

The use of a synchronous demodulator 19 allows for the rejection for all noise except that which occurs at the driving frequency, for instance 1 khz.

The present invention is not limited to the described embodiments herein, but it is envisioned to incorporate numerous means for supplying frequencies within the prescribed ranges.

What is claimed is:

1. A method for measuring the unsteady sedimentation potential of particles in suspension comprising:
   inserting at least a portion of said suspension of particles in a cell, said cell having a first electrode and a second electrode;
   vibrating the entire cells at a frequency in the range between 0.001–50 khz to accelerate said particles in suspension contained therein to cause an unsteady sedimentation of said particles in suspension; and
   measuring the unsteady sedimentation potential of the accelerated particles across said first and second electrodes.

2. The method according to claim 1, wherein said first and second electrodes are disposed at opposite ends of said cell.

3. The method according to claim 1, wherein said cell is vibrated by means of a motor.

4. The method according to claim 3, wherein said motor is a speaker motor.

5. The method according to claim 3, wherein said motor is connected by mechanical linkage to said cell.

6. The method according to claim 3, wherein a mechanical resonator is disposed between said motor and said cell.

7. The method according to claim 3, wherein said mechanical resonator is a tuning fork.

8. The method according to claim 1, wherein said unsteady sedimentation potential across said first and second electrodes is measured by an amplitude detector.

9. The method according to claim 8, wherein said amplitude detector is a synchronous demodulator.

10. The method according to claim 8, wherein said amplitude detector has a detection frequency in the range between 0–50 khz.

11. The method according to claim 8, wherein an amplifier is disposed between said electrodes and said amplitude detector.

12. An apparatus for measuring the unsteady sedimentation potential of particles in a suspension comprising:
   a cell, said cell containing at least a portion of said particles in suspension therein;
   a first electrode and a second electrode disposed within said cell;
   means for vibrating the entire cell at a frequency in the range between 0.0001–50 khz to accelerate said particles in suspension contained therein to cause an unsteady sedimentation of said particles in suspension; and
   means for detecting an unsteady sedimentation potential of the accelerated particles across said first and second electrodes.

13. The apparatus according to claim 12, wherein said first and second electrodes are disposed at opposite ends of said cell.

14. The apparatus according to claim 12, wherein said means for vibrating said cell is a motor.

15. The apparatus according to claim 14, wherein said motor is a speaker motor.

16. The apparatus according to claim 14, wherein said motor is connected by mechanical linkage to said cell.

17. The apparatus according to claim 16, wherein said mechanical linkage is a rod.

18. The apparatus according to claim 14, wherein a mechanical resonator is disposed between said motor and said cell.

19. The apparatus according to claim 18, wherein said mechanical resonator is a tuning fork.

20. The apparatus according to claim 18, wherein said mechanical resonator is connected to said motor by a first mechanical linkage and to said cell by a second mechanical linkage.

21. The apparatus according to claim 20, wherein said first and second mechanical linkages are steel rods.

22. The apparatus according to claim 12, wherein said means for detecting said unsteady sedimentation potential is an amplitude detector.

23. The apparatus according to claim 22, wherein said amplitude detector is a synchronous demodulator.

24. The apparatus according to claim 22, wherein said amplitude detector has a detection frequency in the range between 0–50 khz.

25. The apparatus according to claim 22, wherein an amplifier is disposed between said electrodes and said amplitude detector.

* * * * *